United States Patent [19]

Mrozik

[11] 4,001,406

[45] Jan. 4, 1977

[54] BENZENEDISULFONAMIDES AS ANTHELMINTIC AGENTS

[75] Inventor: Helmut H. Mrozik, Matawan, N.J.

[73] Assignee: Merck & Co., Inc., Rahway, N.J.

[22] Filed: Aug. 25, 1975

[21] Appl. No.: 607,638

Related U.S. Application Data

[60] Continuation-in-part of Ser. No. 477,542, June 2, 1974, abandoned, which is a division of Ser. No. 359,393, May 11, 1973, abandoned.

[52] U.S. Cl. .............................................. 424/228
[51] Int. Cl.$^2$ ........................................ A61K 31/63
[58] Field of Search ........................... 424/228, 321

[56] References Cited

UNITED STATES PATENTS

| | | | |
|---|---|---|---|
| 2,965,656 | 12/1960 | Novello | 424/228 |
| 3,297,693 | 1/1967 | de Stevens et al. | 260/243 D |
| 3,480,652 | 11/1969 | McLamore et al. | 260/397.7 |
| 3,828,078 | 8/1974 | Mrozik | 424/321 |

*Primary Examiner*—V. D. Turner
*Attorney, Agent, or Firm*—David L. Rose; J. Jerome Behan

[57] ABSTRACT

Haloalkyl benzenedisulfonamides are employed in the treatment of both mature and immature liver fluke infections. They are orally or parenterally administered to host animals in suitable compositions.

5 Claims, No Drawings

BENZENEDISULFONAMIDES AS ANTHELMINTIC AGENTS

RELATIONSHIP TO OTHER APPLICATIONS

This application is a continuation-in-part of my application Ser. No. 477,542 filed June 2, 1974 now abandoned which in turn is a divisional application of Ser. No. 359,393 filed May 11, 1973, now abandoned.

SUMMARY OF THE INVENTION

This invention is concerned with a novel method for the treatment of liver fluke infection, also known as fascioliasis, of both the mature and immature varieties. More particularly, it is concerned with the use of 1-amino-haloalkyl-4,6-benzenedisulfonamide compounds as fasciolicides. This invention is also concerned with compositions containing said benzenedisulfonamides for administration to animals infected with mature and immature liver fluke. Further aspects of this invention will become apparent on reading the complete disclosure.

DESCRIPTION OF THE PRIOR ART

Many sulfonamides, especially benzenesulfonamide compounds have been known in the art for many years. They have been generally prepared and studied for their activity as antibacterial and diuretic agents and much data is published concerning the bacteriostactic and diuretic activity of sulfonamide compounds. In addition, certain benzenedisulfonamides have been prepared as intermediates in the preparation of diuretic agents. Benzenedisulfonamides have not, however, received extensive study as anthelmintic agents and have not been described heretofore as having any value in combatting liver flukes or other helmintic parasites.

DESCRIPTION OF THE INVENTION

The compounds which, according to this invention are useful for the treatment of mature and immature liver fluke are represented by the following structural formula:

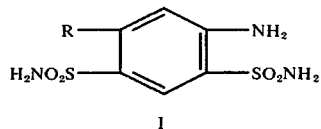

where R is a haloalkyl group of from 2 to 6 carbon atoms containing from one to 13 halogen atoms. The halogen atoms substituted on the alkyl group may be fluorine, chlorine, bromine, or iodine although fluorine and chlorine are preferred. The alkyl chain may be either straight or of a branched configuration. The halogen atoms on a particular perhaloalkyl group need not be all the same. Included in the above definition of R are those groups with a mixture of halogen atoms. The following groups are exemplary of those included in the definition of R. The list is not intended to be restrictive of this invention.

α-Fluoroethyl
β,β,β-Trifluoroethyl
Pentachloroethyl
α,α,β-Trifluoroethyl
Pentafluoroethyl
α,α-Difluoroethyl
α,β,β-Trichloro-α,β-Difluoroethyl
α,α-Difluoro-β,β,β-trichloroethyl
Heptafluoroisopropyl
Heptafluoropropyl
Perchloropentyl
Perfluorobutyl The preferred embodiments of this invention are those halo groups within the definition of R wherein the halogen is fluorine. Especially preferred are those alkyl groups which are fully fluorinated. This is exemplified by pentafluoroethyl and heptafluoropropyl.

Many haloalkyl compounds are attained by a procedure which uses as its starting material an alkyl benzene. The procedure is outlined in the following reaction scheme.

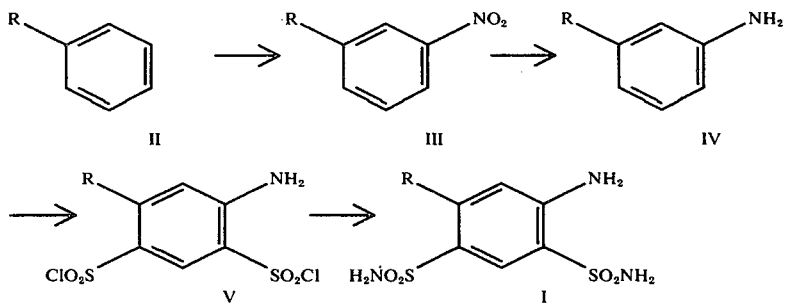

wherein R is as previously defined. The haloalkyl benzene starting material (II) is nitrated affording the m-nitro derivative (III) which is reduced by catalytic hydrogenation affording the m-aniline derivative (IV) which is chlorosulfonated with chlorosulfonic acid and sodium chloride yielding (V). Treatment of V with ammonia produces the product (I). A complete description of the experimental conditions and procedures employed in the above reaction scheme is found in an article by Cragoe et al. found in the Journal of Medicinal and Pharmaceutical Chemistry 5 898 (1962).

The haloalkyl benzene compounds (II) employed as starting materials for the above process are known compounds, and processes for their preparation have been described in the chemical literature.

Where the halogen atoms of the product are fluoro, such compounds may be prepared by an alternate process wherein m-iodoaniline is treated with a fluorinated iodoalkyl compound in the presence of copper powder which has been activated by treatment with iodine and hydrochloric acid. The reaction is run in a polar solvent such as dimethylsulfoxide at a temperature of from 100°–150° C. for from 1 to 10 hours. It is preferred to run the reaction in a sealed vessel such as a pressure bomb under an atmosphere of an inert gas such as nitrogen. The product is isolated by procedures known to those skilled in this art.

The above discussions and references are sufficient for anyone skilled in the art to prepare the compounds of this invention which have been discovered as being potent anthelmintic and fasciolicidal agents.

The compounds of the present invention have utility in the field of animal therapy. They are effective anthelmintics and are especially effective for the prevention and cure of both mature and immature liver fluke of the species *Fasciola gigantica* and *Fasciola hepatica*, the common liver fluke in sheep and cattle. The preferred dosage levels depend on the type of compound to be employed, the type of animal to be treated, the particular helminth to be combatted, the severity of the helminthic infestation and whether prophylactic or curative treatment is desired. In general, effective fluke eradication is achieved when the compounds are administered in a single oral dose at dosage levels of from about 1 to 300 mg/kg of animal body weight and preferably from about 10 to 100 mg/kg of animal body weight. The compounds of the present invention may be administered in a variety of ways depending upon the particular animal employed, the type of anthelmintic treatment normally given to such animal, the materials employed and the particular helminths being combatted. It is preferred to administer them in anthelmintically effective amounts in a single or divided oral or parenteral dose at a time when fascioliasis is apparent of suspected in the animal.

In addition to the inactive ingredients in the composition, said composition may contain one or more other active ingredients which may be selected from the compounds described by formula I or from other known anthelmintic agents. Beneficial results are obtained when the compounds of formula I are combined with an anthelmintic agent such as 2-(4-thiazolyl)benzimidazole (thiabendazole) or tetramisole (dl-2,3,5,6-tetrahydro-6-phenylimidazo[2,1-b]thiazole) or other known anthelmintic agents.

In general, compositions containing the active anthelmintic compound are employed. The amounts of the anthelmintic ingredient in the composition as well as the remaining constituents vary according to the type of treatment to be employed, the host animal and the particular helmintic infestation being treated and whether prophylactic or curative treatment is desired. In general, however, compositions suitable for oral admisistration, containing a total weight percent of the active compound or compounds ranging from 0.01 to 95% will be suitable with the remainder of the compositions being any suitable carrier or vehicle. In general, the lower concentrations employed over prolonged periods are used for prophylactic or preventive purposes. A number of modes of treatment may be employed and each to some extent determines the general nature of the composition. For example, the anthelmintic compounds may be administered to domesticated animals in a unitary oral dosage form such as a tablet, bolus, capsule or drench; a liquid oil base form suitable for parenteral administration, or they may be compounded as a feed premix to be later admixed with the animal food. When the compositions are to be solid unit dosage forms as in tablets, capsules or boluses, the ingredients other than the active compounds may be any other non-toxic vehicle convenient in the preparation of such forms and preferably materials nutritionally suitable such as starch, lactose, talc, magnesium stearate, vegetable gums, and the like. Moreover, when capsules are empoyled, the active compound may be used in essentially undiluted form, the only extraneous material being that of the capsule casing itself which may be hard or soft gelatin or any other orally acceptable encapsulating material. When the dosage form is to be used for parenteral administration, the active material is suitably admixed with an acceptable oil base vehicle preferably of the vegetable oil variety such as peanut oil, cotton seed oil, and the like. In all such forms, that is, in tablets, boluses, capsules, and oil base formulations; the active compound conveniently ranges from about 5 to 95% by weight of the total composition.

When the unit dosage form is to be in the form of a drench, the anthelmintic agents may be mixed with agents which will aid in the subsequent suspending of The active compounds in water such as bentonite, clays, water soluble starches, cellulose derivatives, gums, surface active agents and the like to form a dry pre-drench composition, and this pre-drench composition is added to water just before use. In the pre-drench formulation, in addition to the suspending agent, such ingredients as preservatives, anti-foam compounds, or other suitable diluents or solvents may be employed. Such a dry product may contain as much as 95% by weight of the active compound, the rest being excipient. Preferably, the solid composition contains from 30 to 95% by weight of the active compound. Enough water should be added to the solid product to provide proper dosage level with a convenient amount of liquid for a single oral dose. The commonly used measure in the field is 1 fluid ounce of material and thus that 1 fluid ounce of material should contain enough of the anthelmintic compound to provide an effective dosage level. Liquid drench formulations containing from 10 to 50 % by weight of dry ingredients will, in general, be suitable with a preferred range being from 15 to 25 weight percent.

When the compositions are intended to be used in feeds, feed supplements or feed premixes, they will be mixed with suitable ingredients of the animals nutrient ration. Solid orally ingestible carriers normally used for such purposes such as distillers dried grains, corn meal, citrus meal, fermentation residues, ground oyster sheels, citrus meal, fermentation residues, attapulgus clay, wheat shorts, molasses solubles, corn cob meal, vegetable substances, toasted dehulled soya flour, soya bean meal feed, antibiotic mycellia, soya grits, crushed limestone and the like are all suitable. The active compounds are intimately dispersed or admixed throughout the active solid carrier by methods such as grinding, melting, or tumbling. By selecting a proper diluent and by altering the ratio of carrier to active ingredient, compositions of any desired concentration may be prepared. Feed supplement formulations containing from about 5 to 30% of active ingredient are particularly suitable for addition to feeds. The active compound is normally dispersed or mixed uniformly in the diluent but in some instances may be adsorbed on the carrier.

These supplements are added to the finished animal feed in an amount adequate to give the final conconcentration desired for controlling or treating the helminth infection by way of animal ration. Although the preferred level in feeds will depend on the particular compounds being employed, the active compounds of this invention are normally fed at levels of 0.01 to 3%. As stated above, animals are preferably treated at a time when the infestation is apparent of suspected and the most preferred method of treatment is with oral doses. Thus, administration of medicated feed is not preferred but may be employed. Similarly, the amounts of drug present in the feed may be reduced to levels in the order of 0.01% to 0.05% by weight. based on the weight of the feed and the medicated feed administered over prolonged periods. This could be in the nature of a preventive or prophylactic measure. Another method of administering the compounds of this invention to animals whose feeds are conveniently pelleted such as sheep is to incorporate them directly into the pellets. For instance, the anthelmintic compounds are readily incorporated in the nutritionally adequate alfa pellets at levels of 2 to 10 g. per pound for therapeutic use and lower levels for prophylactic use, and such pellets fed to the animals.

Examples of compositions suitable for administration to animals are:

A typical bolus composition is as follows:
4-Amino-6-pentafluoroethyl-1,3-benzenedisulfonamide: 7.0 g.
dicalcium phosphate: 1.0 g.
starch; 0.7 g.
guar gum; 0.16 g.
talc: 0.11 g.
magnesium stearate: 0.028 g.
A typical drench composition is as follows:
4-Amino-6-(n-heptafluoropropyl)-1,3-benzenedisulfonamide: 5.0 g.
benzalkonium chloride: 0.6 ml.
antifoam emulsion: 0.06 g.
hydroxyethyl cellulose: 0.3 g.
sodium phosphate: 0.3 ml.
water: q. s. to 30 ml.
Examples of typical feed premix supplements are as follows:

| A. | 4-Amino-6-pentafluoroethyl-1,3-benzenedisulfonamide | 10 lbs. |
|---|---|---|
|  | wheat shorts | 90 lbs. |
| B. | 4-Amino-6-α,α,β-trifluoro-β-chloroethyl-1,3-benzene-disulfonamide | 15 lbs. |
|  | ground oyster shells | 40 lbs. |
|  | citrus meal | 45 lbs. |
| C. | 4-Amino-6-pentafluoroethyl-1,3-benzenedisulfonamide | 10 lbs. |
|  | corn meal | 90 lbs. |
| D. | 4-Amino-6-(β,β,β-trifluoro-α,α-dichloroethyl)-1,3-benzenedisulfonamide | 15 lbs. |
|  | wheat shorts | 50 lbs. |
|  | corn meal | 35 lbs. |

The above feed premix supplements are combined with the animals regular feed, intimately mixing therewith such that the final concentration of the active ingredient is from 0.01 to 3% by weight.

EXAMPLE 1

4-Amino-6-Pentafluoroethyl-1,3-Benzenedisulfonamide

A. m-Nitro-pentafluoroethylbenzene

74 G. (0.4 moles) of pentafluoroethylbenzene is cooled to 5° C. and treated dropwise with a mixture of 22 g. (0.33 moles) of concentrated nitric acid and 33 g. (0.32 moles) of concentrated sulfuric acid. The temperature is maintained at 5°–15° C. during the 1 hour addition period and then raised to 45° C. for 1 hour. The reaction mixture is cooled and poured onto ice. The aqueous mixture is extracted with ether, the ether extracts washed with water, dried over sodium sulfate, and the residue is distilled at 0.35 mm. of Hg at 74°–75° C. The yield is 84 g. (87%) of m-nitro-pentafluoroethylbenzene.

B. m-Pentafluoroethylaniline

110 G. (0.457 moles) of m-nitropentafluoroethylbenzene in 450 ml. of ethanol is hydrogenated for 5 hours at 162 kg/cm$^2$ at 30°C. in the presence of Raney Nickel. The residue is removed by filtration and the filtrate evaporated to dryness and distilled at 14 mm. of Hg at 80°–82° C. affording 87 g. (95%) of m-pentafluoroethylaniline.

C. 4-Amino-6-pentafluoroethyl-1,3-benzenedisulfonamide

20 G. (0.095 moles) of m-pentafluoroethylaniline is added over a 20 minute period under anhydrous conditions to 177 g. (100 ml., 1.52 moles) of chlorosulfonic acid. 90 G. (1.55 moles) of sodium chloride is added portionwise over a 90 minute period. The temperature is slowly raised to 150° C. and maintained at that point for 2 hours. The reaction mixture is cooled, 500 ml. of ice water is added, and the aqueous mixture extracted with ether. The ether extract is washed with water, dried over sodium sulfate, concentrated to a volume of 100 ml. and added to 250 ml. of liquid ammonia. The liquid ammonia is allowed to evaporate and the solid material triturated with boiling benzene and recrystallized from water, affording 19.7 g. (56%) of 4-amino-6-pentafluoroethyl-1,3-benzenedisulfonamide, m.p. 247°–248° C.

When in the above procedure there is employed heptafluoropropylbenzene; heptafluoroisopropylbenzene; β,β,β-trifluoroethylbenzene; α,β,β-trichloro-α,β-difluoroethylbenzene; α,α-difluoro-β,β,β-trichloroethylbenzene or α,α-difluoroethylbenzene in place of pentafluoroethyl-benzene there is obtained 4-amino-6-heptafluoropropyl-1,3-benzenedisulfonamide; 4-amino-6-heptafluoroisopropyl-1,3-benzenedisulfonamide; 4-amino-6-(β,β,β-trifluoroethyl)-1,3-benzenedisulfonamide; 4-amino-6-(α,β,β-trichloro-α,β-difluoroethyl)-1,3-benzenedisulfonamide; 4-amino-6-(α,α-di-fluoro-β,β,β-trichloroethyl)-1,3-benzenedisulfonamide; and 4-amino-6-(α,α-difluoroethyl)-1,3-benzenedisulfonamide respectively.

EXAMPLE 2

4-Amino-6-Heptafluoropropyl-1,3-Benzenedisulfonamide

A. m-Heptafluoropropylaniline

Commercial Copper Powder is activated by treating 100 g. with one liter of a 2% solution of iodine in acetone for 5 to 10 minutes at room temperature. The solid material is filtered and stirred with 500 ml. of a 50% solution of concentrated hydrochloric acid in acetone. The activated Copper Powder is filtered, washed with acetone, and dried in vacuo at room temperature.

35.2 G. (17.5 ml., 0.118 moles) of heptafluoropropyliodide, 28.8 g. of activated Copper Powder and 25.0 g. (0.114 moles) 3-iodoaniline are combined with 142 ml. dimethylsulfoxide in a glass liner for a steel bomb. The bomb is sealed under 60 lbs. of nitrogen and heated at 120° C. for 3½ hours with rocking. The bomb is allowed to come to room temperature and the reaction mixture is filtered, washed with 10 ml. of dimethylsulfoxide and 50 ml. of ether. The combined filtrate and washings are added to 250 ml. of water and extracted with 500 ml. of ether. The ether extract is washed with 100 ml. of water. The water layer back-extracted with 250 ml. of ether and the combined ether layers dried over magnesium sulfate. The ether is evaporated at atmospheric pressure and the residue distilled at 7 mm. of Hg at 78° C. affording 20.5 g. of m-heptafluoropropylaniline.

B. 4-Amino-6-heptafluoropropyl-1,3-benzenedisulfonamide

Following the procedures of Example 1C utilizing 3.0 g. of m-heptafluoropropylaniline, 40 ml. of chlorosulfonic acid, 40 g. of sodium chloride, and 50 ml. of liquid ammonia there is obtained 4-amino-6-heptafluoropropyl-1,3-benzenedisulfonamide, m.p. 259°–262° C.

When in the above procedure there is employed 2-iodo-heptafluoropropane; 1-iodo-perfluoroheptane; or α-iodo-α,α,β-trifluoro-β-chloroethane is employed in place of heptafluoropropyliodide there is obtained 4-amino-6-heptafluoroisopropyl-1,3-benzenedisulfonamide; 4-amino-6-(perfluoroheptyl)-1,3-benzenedisulfonamide; and 4-amino-6-(α,α,β-trifluoro-β-chloroethyl)-1,3-benzenedisulfonamide; respectively.

What is claimed is:

1. A method for curing fascioliasis which comprises administering to an animal so infected a fasciolicidally effective amount of a compound having the formula:

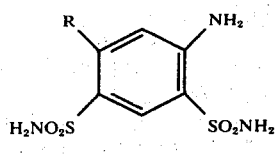

wherein R is a haloalkyl group of from 2 to 6 carbon atoms containing from 1 to 13 halogen atoms.

2. The method of claim 1 wherein the compound administered is 4-amino-6-perfluoroalkyl-1,3-benzenedisulfonamide.

3. The method of claim 1 wherein the compound administered is 4-amino-6-pentafluoroethyl-1,3-benzenedisulfonamide.

4. The method of claim 1 wherein the compound administered is 4-amino-6-heptafluoropropyl-1,3-benzenedisulfonamide.

5. The method of claim 1 wherein the compound administered is 4-amino-6-(α,α-difluoro-β,β,β-trichloroethyl)-1,3-benzenedisulfonamide.

* * * * *